(12) United States Patent
Weiger (10) Patent No.: US 9,320,418 B2
(45) Date of Patent: Apr. 26, 2016

(54) ENDOSCOPE WITH ADJUSTABLE ILLUMINATION DIRECTION

(71) Applicant: Karl Storz GmbH & Co. KG, Tuttlingen (DE)

(72) Inventor: Ulrich Weiger, Kolbingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 293 days.

(21) Appl. No.: 13/891,572

(22) Filed: May 10, 2013

(65) Prior Publication Data

US 2013/0322109 A1 Dec. 5, 2013

Related U.S. Application Data (63) Continuation of application No. PCT/EP2011/005682, filed on Nov. 11, 2011.

(30) Foreign Application Priority Data

Nov. 11, 2010 (DE) .......................... 10 2010 050 931

(51) Int. Cl.
*A61B 1/06* (2006.01)
*A61B 1/00* (2006.01)

(52) U.S. Cl.
CPC ............... *A61B 1/06* (2013.01); *A61B 1/00096* (2013.01); *A61B 1/00183* (2013.01); *A61B 1/0623* (2013.01)

(58) Field of Classification Search
CPC ...... A61B 1/06; A61B 1/0623; A61B 1/0676; A61B 1/00183; A61B 1/00096
See application file for complete search history.

(56) References Cited

U.S. PATENT DOCUMENTS

| 4,398,811 | A | 8/1983 | Nishioka et al. |
| 4,718,417 | A | 1/1988 | Kittrell et al. |
| 6,638,216 | B1 * | 10/2003 | Durell ........................... 600/173 |
| 2010/0022838 | A1 | 1/2010 | Hoeg |
| 2012/0035421 | A1 * | 2/2012 | Weiger ......................... 600/173 |

FOREIGN PATENT DOCUMENTS

| DE | 60015375 T2 | 2/2006 |
| EP | 1273274 A1 | 1/2003 |
| WO | 0139657 A1 | 6/2001 |
| WO | 02096478 A2 | 12/2002 |
| WO | 2009053989 A2 | 4/2009 |

OTHER PUBLICATIONS

International Search Report Application No. PCT/EP2011/005682 Completed: Mar. 8, 2012; Mailing Date: Mar. 21, 2012 3 pages.

* cited by examiner

*Primary Examiner* — Stephen F Husar
(74) *Attorney, Agent, or Firm* — Whitmyer IP Group LLC (57) ABSTRACT

An endoscope having an adjustable illumination direction includes a reflective surface reflecting illumination light for the illumination of an object observed by means of the endoscope, the reflective surface being moveable in order to adjust the illumination direction.

8 Claims, 3 Drawing Sheets

ENDOSCOPE WITH ADJUSTABLE ILLUMINATION DIRECTION

FIELD OF THE INVENTION

The present invention relates to an endoscope having an adjustable illumination direction.

BACKGROUND OF THE INVENTION

Besides endoscopes for medical and non-medical technical applications, the viewing direction of which is parallel to the longitudinal axis of the shaft of the endoscope, endoscopes having different fixed viewing directions were developed early on. Here and in what follows, the viewing direction of an endoscope always means the direction from the distal end of the endoscope in which an object, which appears in the middle of the image acquired by means of the endoscope, lies. In many applications, however, a fixed viewing direction is disadvantageous. In the least favorable case, for example, the endoscope must be changed several times during a medical intervention. In such cases, the use of an endoscope having an in-situ adjustable or variable viewing direction is advantageous.

The observation of an object in a cavity by means of an endoscope generally requires illumination of the object. To this end, for example, an endoscope comprises light waveguides, in particular glass fibers, by means of which illumination light is transmitted from the proximal end of the endoscope along the shaft to the distal end of the endoscope. Light exit surfaces of the light waveguides at the distal end of the endoscope are arranged and formed in such a way that the entire field of view, or viewing field, is illuminated sufficiently.

In an endoscope having an adjustable viewing direction, in the simplest case the illumination light is distributed at the distal end of the endoscope in such a way that the entire field of view is illuminated independently of the respectively adjusted viewing direction. This, however, entails a number of disadvantages. In particular, light power is wasted, because the entire fields of view of all adjustable illumination directions are constantly illuminated, independently of the actually adjusted viewing direction. For a predetermined desired brightness, a significantly higher light power must therefore be provided overall than in an endoscope having a fixed viewing direction.

Another disadvantage is based on the fact that high-intensity illumination light can damage tissue or other objects photothermally or photochemically. In an endoscope having a fixed viewing direction, too small a distance of the distal end of the endoscope from an object is generally apparent, at least when observing the acquired image. When using a camera on the endoscope, automatic warning of users is also possible when the brightness of an acquired image exceeds a predetermined threshold. In an endoscope having an adjustable viewing direction, however, a part of the illumination light strikes objects which lie outside the field of view. Undesired proximity of the distal end of the endoscope to these objects, and resulting exposure of these objects to a radiation power which is too high, are therefore not apparent.

Another disadvantage is that illumination light which is emitted outside the field of view can also be scattered or reflected by objects or opaque media. The reflected or scattered illumination light may directly or indirectly enter the observation beam path. Contrasts and, above all, the distinguishability of objects in dark image regions can thereby be reduced.

Another disadvantage is due to the fact that the illumination strength or intensity of the illumination light is essentially constant in the direction in which the viewing direction can be varied (also referred to as the vertical direction), while in the direction perpendicular thereto (also referred to as the horizontal direction) it generally decreases slightly toward the edge of the field of view. From endoscopes having a fixed viewing direction, however, users are generally used to an illumination strength which decreases slightly toward the edge of the field of view both in the horizontal direction and in the vertical direction. The constant illumination strength in the vertical direction can therefore be perceived as irritating.

DE 600 15 375 T2 describes an arrangement of a plurality of prisms. One of the prisms can be rotated about an axis in order to shine illumination light in an adjustable viewing direction. The inventors of the present invention have, however, established that the mounting of the rotatable prism is in many cases elaborate in terms of design and production.

SUMMARY OF THE INVENTION

It is an object of the present invention to provide an improved endoscope having an adjustable illumination direction.

Refinements are specified in the dependent claims.

An endoscope having an adjustable illumination direction comprises a reflective surface for reflecting illumination light for the illumination of an object observed by means of the endoscope, the reflective surface being moveable in order to adjust the illumination direction.

The endoscope is, in particular, formed in order to pivot the viewing direction and the illumination direction together. The viewing direction is the direction in which an object, which appears in the middle of an acquired image during observation through the endoscope, lies relative to the distal end of the endoscope. The illumination direction is the average direction, relative to the distal end of the endoscope, in which the illumination light is emitted. In particular, the illumination direction and the viewing direction correspond to one another. Alternatively, the viewing direction and the illumination direction can be adjusted independently of one another or the illumination direction can be varied relative to the viewing direction within predetermined limits, for example in order to achieve full illumination of the observed region in the case of a small object width.

The viewing direction and the illumination direction of the endoscope can, in particular, be pivoted about one or two (in particular parallel) pivot axes, perpendicular to the longitudinal axis of the shaft of the endoscope. The longitudinal axis of the endoscope is, in particular, the longitudinal axis of the shaft. In the case of a rigid straight shaft, the longitudinal axis of the shaft is the straight line on which the midpoints of the cross-sectional surfaces of the shaft lie. In the case of a flexible shaft, the longitudinal axis of the endoscope is the longitudinal axis of the distal end of the shaft, i.e. the straight line on which midpoints of the cross-sectional surfaces of the shaft lie close to its distal end.

The endoscope may be formed in such a way that displacement of the reflective surface entails pivoting of the reflective surface. Displaceability of the reflective surface in the context of this application, however, does not include simple pivotability about an axis lying at the distal end of the endoscope in its shaft.

An endoscope as described here comprises, in particular, a linear guide for guiding the moveable reflective surface along a straight or curved path.

A moveable reflective surface can be guided precisely by a linear guide. A straight or curved linear guide may, for example, be produced with little outlay, as well as greatly miniaturized, with one or more grooves or webs. The linear guide may be configured in such a way that it demands only a small installation space. As an alternative or in addition, the moveable reflective surface may be guided by means of one or more bars, coupling rods, sliding blocks or cross-heads or by means of one or more other couplers, in order to be moveable along a straight or curved path.

Particularly when actuating an optical device at the distal end of the endoscope for adjusting the viewing direction by means of a compression or tension rod in the shaft of the endoscope, the movement of this compression or tension rod can be transmitted with little mechanical outlay onto the moveable reflective surface. In the simplest case, the moveable reflective surface is mechanically coupled directly to the compression or tension rod. The outlay of mechanical gearing, required for example for converting a linear movement into a rotational or pivoting movement, can therefore be substantially or fully obviated.

The moveable reflective surface is, in particular, curved. Examples of a curved configuration of the moveable reflective surface are explained below.

In an endoscope as described here, the reflective surface may be moveable in a direction which makes an angle of not more than 45 degrees with the longitudinal axis of the endoscope.

In particular, the direction in which the reflective surface is moveable differs from the longitudinal axis of the endoscope by no more than 30 degrees or no more than 20 degrees, or is parallel or essentially parallel to the longitudinal axis of the endoscope. A small angle between the direction in which the reflective surface is moveable and the longitudinal axis of the endoscope permits mechanical driving with little outlay. In particular, the reflective surface may be coupled to the aforementioned compression or tension rod directly or merely by means of a simple flexible element. If the direction in which the reflective surface is moveable is parallel or essentially parallel (at most 10 degrees, in particular at most 5 degrees) to the longitudinal axis of the endoscope, then the reflective surface may for example be fastened directly to and guided by the compression or tension rod. An adjustable illumination direction can thus be achieved in a simple and economical way.

In an endoscope as described here, the reflective surface may be moveable along a straight path.

The advantages mentioned in the preceding paragraph apply in particular when the reflective surface is moveable along a straight path. Yet even if the reflective surface is moveable along a straight path which is not parallel to the longitudinal axis of the endoscope, displaceability along a straight path may be advantageous. In particular, straight rails, webs or grooves or other linear guides may be produced simply and permit guiding without play.

In an endoscope as described here, as an alternative, the reflective surface may be moveable along a curved path which has a local center of curvature that at least either is dependent on the position of the reflective surface on the curved path or lies outside the shaft of the endoscope.

Besides one or more curved sections, the curved path may comprise one or more straight sections. The curved path, or a curved section of the path, may be in the form of a circle arc and therefore have a single center of curvature. Alternatively, the curved path or a curved section of the path may have a position-dependent curvature and a position-dependent center of curvature. In particular, the curved path lies in a plane which is perpendicular to a pivot axis of the viewing direction of the endoscope and, in particular, parallel to all viewing directions of the endoscope.

A curved path can amplify the effect on the illumination direction of displacing the reflective surface. Furthermore, a curved path can favor miniaturizability. In particular, a collision of the reflective surface with other devices at the distal end of the endoscope can be avoided by the curvature of the path, or a curved path may have a greater length than a straight path under the spatially restricted conditions at the distal end of the endoscope.

An endoscope as described here may be formed in order to shine illumination light onto the moveable reflective surface from a direction which is not parallel to the longitudinal axis of the endoscope. If the illumination light striking the moveable reflective surface is not collimated, the direction of the illumination light is the average direction of the illumination light bundle striking the moveable reflective surface. The direction from which the endoscope is designed to shine the illumination light onto the moveable reflective surface is, in particular, perpendicular or essentially perpendicular to the longitudinal axis of the endoscope, or makes an angle of at least 45 degrees or at least 60 degrees or at least 75 degrees therewith. In particular, the reflective surface is moveable parallel or essentially parallel to the longitudinal axis of the endoscope and the endoscope is designed to shine illumination light onto the moveable reflective surface from a direction perpendicular to the longitudinal axis of the endoscope.

An endoscope as described here may comprise a light exit surface for exposure of the moveable reflective surface to illumination light, the surface normal of the light exit surface being not parallel to the longitudinal axis of the endoscope and not parallel to a pivot axis of the illumination direction or to a pivot axis of the viewing direction.

The light exit surface is, in particular, a light exit surface of a light guide, of a light source, of a prism or of another transparent body for directing or deviating the illumination light. If the light exit surface is curved, the surface normal of the light exit surface means in particular the average surface normal of the light exit surface. In particular, the surface normal of the light exit surface makes an angle of at least 45 degrees or at least 60 degrees or at least 75 degrees with the longitudinal axis of the endoscope. The surface normal of the light exit surface makes an angle which is at least 45 degrees or at least 60 degrees or at least 75 degrees with the pivot axis of the illumination direction and/or with the pivot axis of the viewing direction. In particular, the surface normal of the light exit surface is perpendicular or essentially perpendicular at least either to the longitudinal axis of the endoscope, to the pivot axis of the illumination direction or to the pivot axis of the viewing direction.

In an endoscope as described here, a line of intersection of the moveable reflective surface with a plane which is parallel to two adjustable illumination directions of the endoscope may be convexly curved.

A convex curvature of the line of intersection can permit modification of the illumination direction by displacement of the reflective surface in the plane parallel to the two adjustable illumination directions. The moveable reflective surface may likewise be curved in a direction perpendicular to the plane parallel to the two adjustable illumination directions. In particular, the moveable reflective surface has a negative Gaussian curvature K, and thus has the configuration of a saddle surface. Relative to a direction perpendicular to the plane parallel to the two adjustable illumination directions, the moveable reflective surface may therefore have an effect which reduces the divergence of the illumination light or increases the convergence of the illumination light. In this way, it is possible to reduce the width (measured in a direction perpendicular to the plane parallel to the two adjustable illumination directions) of an exit window for the illumination light.

As an alternative, the line of intersection of the moveable reflective surfaces with a plane which is parallel to two adjustable illumination directions of the endoscope is concavely curved. Furthermore, the line of intersection may be partially curved convexly and/or partially curved concavely.

A concave curvature of the line of intersection can also make it possible to adjust the illumination direction by displacement of the reflective surface in the plane parallel to the two adjustable illumination directions.

In an endoscope as described here, the moveable reflective surface may comprise a first section and a second section, with at least either the first section and the second section merging non-smoothly into one another or the section lines of the first section and the second section being oppositely curved with a plane which is parallel to two adjustable illumination directions of the endoscope.

In particular, the first section and the second section of the moveable reflective surface are provided for different angle ranges of the illumination direction. For example, illumination light is shone in illumination directions within a first angle range when it strikes the first section of the moveable reflective surface, and in illumination directions within a second angle range when it strikes the second section of the moveable reflective surface.

In particular, the first angle range and the second angle range are contiguous or overlap (in particular slightly). Segmentation of the reflective surface into a plurality of sections, which merge non-smoothly into one another or which are oppositely curved, can permit a larger overall angle range of the adjustable illumination directions. The first section and the second section merge non-smoothly into one another when there is a discontinuity, step or a bend between the first section and the second section, that is to say when the reflective surface is not continuously differentiable, or not differentiable, between the first section and the second section.

In a method for adjusting the illumination direction of an endoscope, a reflective surface for reflecting illumination light for the illumination of an object observed by means of the endoscope is provided. The reflective surface is displaced in order to adjust the illumination direction.

In the method, the reflective surface is guided, in particular, by a straight or curved linear guide.

In the method, in particular, illumination light is shone onto the reflective surface from a direction which is not parallel to the longitudinal axis of the endoscope and not parallel at least either to a pivot axis of the viewing direction or to a pivot axis of the illumination direction.

The method may, in particular, be carried out with an endoscope as described here.

BRIEF DESCRIPTION OF THE DRAWINGS

Embodiments will be explained in more detail below with the aid of the appended figures, in which.

DETAILED DESCRIPTION OF THE INVENTION

Figure 1:
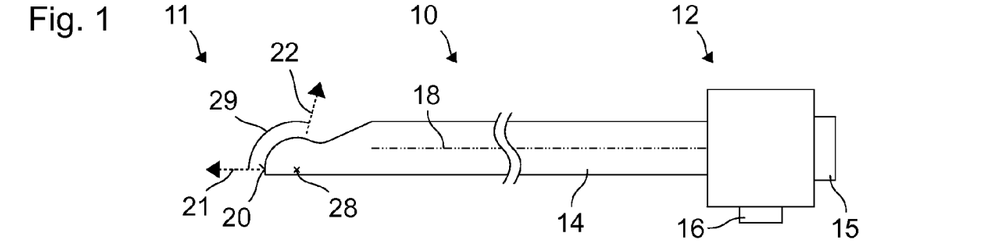
FIG. 1 shows a schematic representation of an endoscope having an adjustable viewing direction.

FIG. 1 shows a schematic representation of an endoscope 10 having a distal end 11, a proximal end 12, and a rigid shaft 14 which extends from the distal end 11 to the proximal end 12. Alternatively, the shaft 14 is flexible or partially flexible. The cross section of the shaft 14, or at least the outer contour of the cross section of the shaft 14, is constant or essentially constant between the distal end 11 and the proximal end 12. In particular, the contour of the cross section of the shaft 14 is circular or elliptical. In this case, the longitudinal axis 18 of the endoscope 10, as represented in FIG. 1, is the symmetry axis of the lateral surface of the shaft 14 between the distal end 12 and the proximal end 11. In the case of a cylindrical lateral surface of the shaft 14, the longitudinal axis 18 is also the set of midpoints or area centroids of the cross sections of the shaft 14 between the distal end 12 and the proximal end 11.

At the distal end 12, the configuration of the shaft 14 departs from cylindrical symmetry, as represented by way of example in FIG. 1. In particular, the shaft 14 has, at the distal end 12, an opening which is closed, in particular hermetically tightly closed, by a transparent window component having a curved surface 20. The surface 20 of the window component has, for example, the configuration of a section of a circular-cylindrical lateral surface, the symmetry axis of the circular cylinder being perpendicular to the longitudinal axis 18 of the endoscope 10 and to the plane of the drawing of FIG. 1. Alternatively, the surface 20 of the transparent window component has the configuration of a section of a spherical surface or of a rotationally symmetrical or rotationally non-symmetrical ellipsoid. The window component is part of the observation and/or illumination beam path. Separate window components may be provided for the observation beam path and one or more illumination beam paths.

At the distal end 12 of the endoscope 10, optical devices (not represented in FIG. 1) which permit variation of the viewing direction between a first extreme viewing direction 21 and a second extreme viewing direction 22 are arranged in the shaft 14. The viewing direction is respectively the direction relative to the distal end 12 of the endoscope 10 in which an object, which appears in the middle of an image acquired by means of the endoscope 10, lies.

In the example represented in FIG. 1, the first extreme viewing direction 21 is parallel or essentially parallel to the longitudinal axis 18 of the endoscope 10. Between the extreme viewing directions 21, 22, there is an angle range 29, which covers approximately 120° in the example represented. The viewing direction of the endoscope 10 is adjustable, in particular continuously, within this angle range.

Devices for adjusting the illumination direction will be explained below with the aid of FIGS. 2 to 7. The illumination direction is in particular identical to the viewing direction, or differs only slightly therefrom. Alternatively, the illumination direction and the viewing direction may be adjusted independently of one another, or an angle difference may be adjusted between them. For the sake of simplicity, only the illumination direction will be discussed below, the illumination direction and the viewing direction being regarded as equivalent.

At the proximal end 11, the endoscope 10 has a first coupler 15 for optical coupling of the endoscope 10 to a camera or an eyepiece, and a second coupler 16 for coupling the endoscope 10 to a light source via a light guide cable. From the second coupler 16, one or more light guides 30 lead through the shaft 14 to the distal end 11 of the endoscope 10. Illumination light generated by a light source can be transmitted via a light guide cable, the second coupler 16 and the light guide or guides 30 to the distal end 11 of the endoscope 10.

Figure 2:
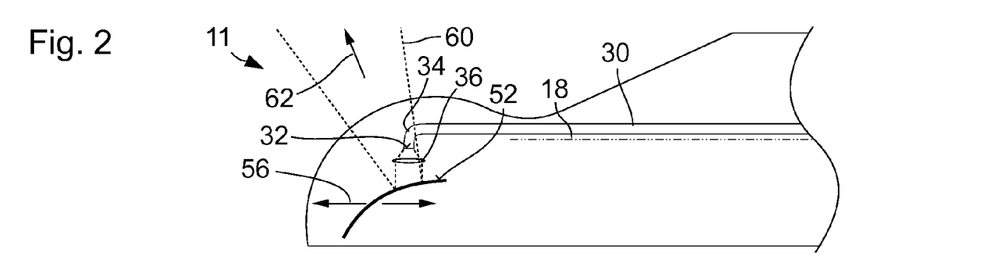
FIG. 2 shows a schematic representation of the distal end of an embodiment of an endoscope.
Figure 3:
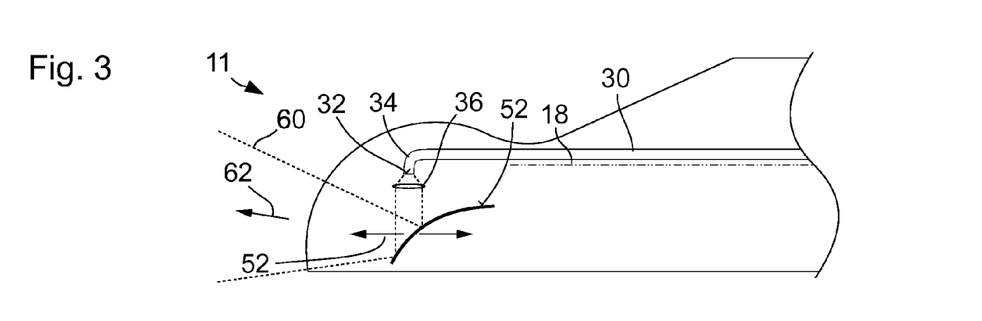
FIG. 3 shows a further schematic representation of the distal end of FIG. 2.

FIGS. 2 and 3 show schematic cross-sectional representations of an embodiment of the distal end 11 of an endoscope, for example of the endoscope 10 explained above with the aid of FIG. 1. The cross-sectional plane represented is parallel to the longitudinal axis 18, shown in FIG. 1, of the endoscope 10. In the shaft of the endoscope, a light guide 30 extends from the second coupler 16, shown in FIG. 1, to the distal end 11 of the endoscope 10. At the distal end 11, the light guide 30 has a light exit surface 32 and, immediately optically upstream of the light exit surface 32, a curvature 34. At the curvature 34, the light guide 30 changes its direction, that is to say the direction in which it guides or transmits illumination light, by about 90 degrees.

A lens 36 is arranged optically downstream of the light exit surface 32 of the light guide 30, and against the light exit surface 32. The lens 36 in the example shown in FIGS. 2 and 3 is a converging lens, which reduces the divergence of the illumination light emerging from the light exit surface 32 of the light guide 30. In particular, the lens 36 is formed and arranged as a collimator so that, optically downstream of the lens 36, the illumination light is aligned essentially parallel and essentially has a constant beam cross section. Instead of a single lens, it is also possible to provide a plurality of lenses, or an objective, or one or more mirrors or a diffraction grating.

A moveable curved reflective surface 52, in particular a moveable curved mirror, is arranged optically downstream of the lens 36. The curved reflective surface 52 is moveable in a direction which is indicated by arrows 56 in FIGS. 2 and 3. In particular, the curved reflective surface 52 is moveable along a straight path. In particular, the curved reflective surface 52 is moveable in a direction 56 parallel to the longitudinal axis 18 of the endoscope 10. Alternatively, the curved reflective surface 52 may be moveable along a straight path which is not parallel to the longitudinal axis 18 of the endoscope 10, or along an at least partially curved path. A curved path, along which the curved reflective surface 52 is moveable, has in particular a position-dependent center of curvature and/or at least one center of curvature which lies outside the pivot axis 28 of the viewing direction 21, 22.

In FIGS. 2 and 3, the moveable curved reflective surface 52 is represented in two different positions. Edges or contours of illumination light cones, which emerge from the light exit surface 32 of the light guide 30, are indicated by dashed lines 60 in both of FIGS. 2 and 3. Although light cones cannot be sharply delimited merely owing to diffraction effects, the dashed lines 60 indicate the propagation of the illumination light in a way which is recognizable to those skilled in the art.

By comparing FIGS. 2 and 3, it can be seen that illumination light emerging from the light exit surface 32 is directed in different directions 62 and solid angle ranges owing to the curvature of the reflective surface 52 as a function of the position of the curved reflective surface 52.

In the distal position, shown in FIG. 2, of the curved reflective surface 52, the illumination light collimated by the lens 36 is reflected by a region of the reflective surface 52, the surface normals of which make a large angle with the longitudinal axis 18 of the endoscope 10. Correspondingly, the illumination light is shone into a solid angle range which differs greatly from the direction of the longitudinal axis 18 of the endoscope 10.

In the position, shown in FIG. 3, of the moveable curved reflective surface 52, the illumination light collimated by the lens 36 strikes a region of the reflective surface 52 in which the local surface normals of the reflective surface 52 make a much smaller angle with the longitudinal axis 18 of the endoscope 10. Correspondingly, the illumination light is shone into a solid angle range whose center lies close to the direction of the longitudinal axis 18 of the endoscope 10. Since the moveable curved reflective surface 52 is smooth, any desired illumination direction 62 within a predetermined interval can be adjusted by displacing the curved reflective surface 52.

Figure 4:
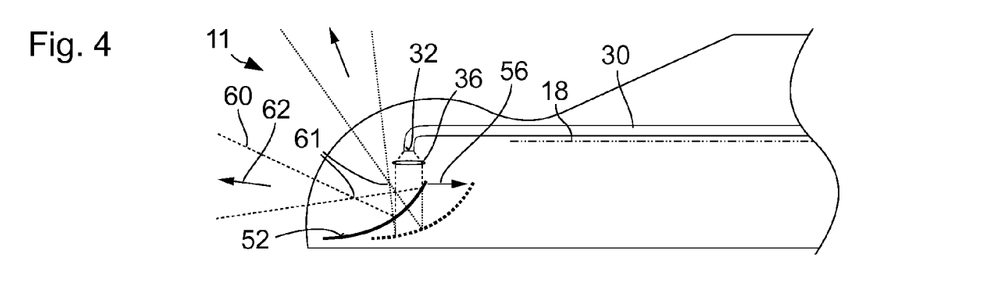
FIG. 4 shows a schematic representation of the distal end of another embodiment of an endoscope.

FIG. 4 shows a schematic cross-sectional representation of another embodiment of the distal end 11 of an endoscope, for example of the endoscope 10 explained above with the aid of FIG. 1. In some features, the embodiment of FIG. 4 resembles the embodiment of FIGS. 2 and 3. The embodiment of FIG. 4 differs from the embodiment of FIGS. 2 and 3 particularly in that the moveable curved reflective surface 52 is shaped concavely instead of convexly.

Two different possible positions of the moveable curved reflective surface 52 are represented in FIG. 4, one by a solid line and one by a dashed line. In the position in which the moveable curved reflective surface 52 is represented as a solid line, the illumination light emerging from the light exit surface 32 of the light guide 30 and collimated by the lens 36 is shone by the moveable curved reflective surface 52 in an average direction, or an illumination direction 62, which makes a small angle with the longitudinal axis 18 of the endoscope 10. In the position of the moveable curved reflective surface in which it is represented by dashes, the illumination light emerging from the light exit surface 32 of the light guide 30, collimated by the lens 36 and reflected by the moveable curved reflective surface 52 is shone into a solid angle range and in a direction which makes a large angle with the longitudinal axis 18 of the endoscope 10.

Owing to the concave configuration of the moveable curved reflective surface 52, the illumination light cone 60 has a constriction 61 for both positions of the moveable curved reflective surface 52. The constriction 61 is represented in an idealized way in the form of a point in FIG. 4. In reality, the constriction 61 has a finite extent merely because of the diffraction limitation and the extent of the light exit surface 32 of the light guide 30.

Figure 5:
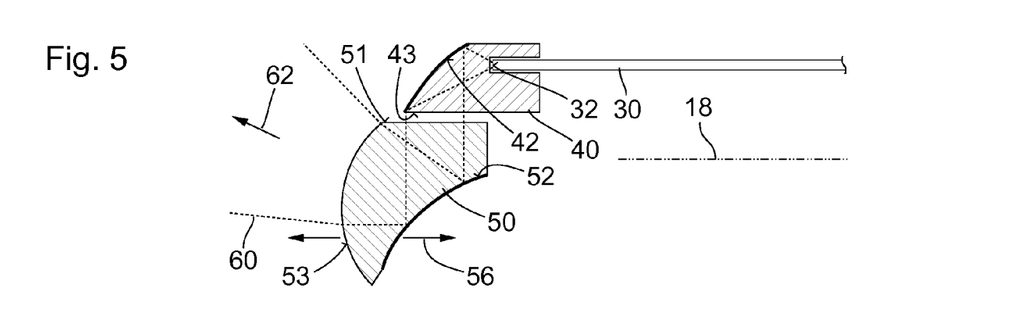
FIG. 5 shows a schematic representation of the distal end of another embodiment of an endoscope.

FIG. 5 shows a schematic representation of another embodiment of the distal end of an endoscope, in particular of the endoscope 10 explained above with the aid of FIG. 1. In contrast to FIGS. 2 to 4, only devices which guide or convey the illumination light are shown in FIG. 5. The contour of the shaft of the endoscope 10 and the other devices are not shown in FIG. 5.

In the embodiments explained above with the aid of FIGS. 2 to 4, the surface normals of the light exit surfaces 32 of the light guides 30 are essentially perpendicular to the longitudinal axis 18 of the endoscope 10. In contrast thereto, in the embodiment of FIG. 5, the light guide is essentially straight and the surface normal of the light exit surface 32 is essentially parallel to the longitudinal axis 18 of the endoscope 10. The illumination light emerging from the light exit surface 32 of the light guide 30 is coupled into a fixed transparent body 40. In particular, the light exit surface 32 of the light guide 30 is adhesively bonded, cemented or welded to the transparent body. In the example shown in FIG. 5, the distal end of the light guide 30 is furthermore arranged in a bore of the transparent body 40.

The transparent body 40 has a reflective surface 42. The reflective surface reflects owing to total reflection or owing to a reflective coating. The reflective surface 42 is formed and arranged in order to direct the illumination light emerging from the light exit surface 32 of the light guide 30 in a direction essentially perpendicular to the longitudinal axis 18 of the endoscope 10. In particular, the reflective surface 42 of the transparent body 40 is curved in order to collimate the illumination light. To this end, the reflective surface 42 of the transparent body 40 has, in particular, the configuration of a section of a paraboloid of rotation.

The transparent body 40 furthermore has a light exit surface 43 through which the illumination light emerging from the light exit surface 32 of the light guide 30 and reflected at the reflective surface 42 of the transparent body 40 emerges in a direction essentially perpendicular to the longitudinal axis 18 of the endoscope 10. In the example represented, the light exit surface 43 of the fixed transparent body 40 is planar and has a surface normal which is essentially perpendicular to the longitudinal axis 18 of the endoscope 10.

A light entry surface 51 of a moveable transparent body 50 is arranged facing the light exit surface 43 of the fixed transparent body 40. The light exit surface 43 of the fixed transparent body and the light entry surface 51 of the moveable transparent body 50 are, in particular, mutually parallel and respectively planar. The moveable transparent body 50 furthermore has a curved reflective surface 52 and a light exit surface 53, which is likewise curved in the example represented.

For example, the curved reflective surface 52 of the moveable transparent body 50 reflects illumination light owing to total reflection or owing to a reflective coating. The curved reflective surface 52 is arranged on a section of the surface of the moveable transparent body 50 which is concave at least relative to the cross-sectional plane represented in FIG. 5. Relative to the spatial region in which illumination light propagates, the reflective surface 52 is convexly curved.

The transparent body 50 is moveable in a direction, indicated by arrows 56, parallel or essentially parallel to the longitudinal axis 18 of the endoscope 10. Similarly as in the embodiments of FIGS. 2 and 3, the illumination light reflected by the moveable reflective surface 52 is shone into different solid angle ranges depending on the position of the transparent body 50 and the position of the curved reflective surface 52. For the represented central position of the moveable transparent body 50, the propagation of the illumination light emerging from the light exit surface 32 of the light guide 30 is qualitatively indicated by contours of an illumination light cone 60, in a similar way as in FIGS. 2 to 4.

Figure 6:
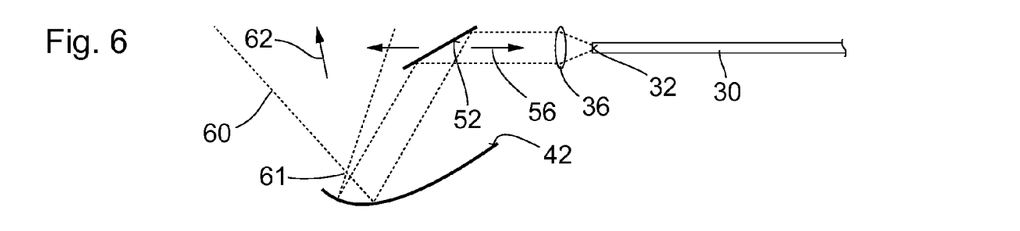
FIG. 6 shows a schematic representation of the distal end of another embodiment of an endoscope.
Figure 7:
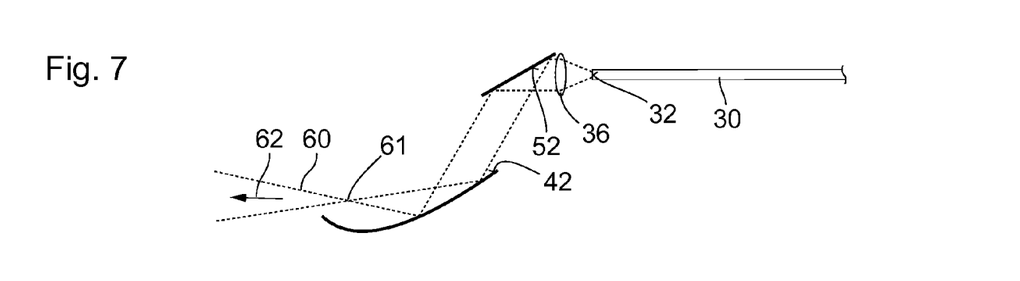
FIG. 7 shows a further schematic representation of the distal end of FIG. 6.

FIGS. 6 and 7 show schematic representations of another embodiment of the distal end of an endoscope, for example of the endoscope 10 explained above with the aid of FIG. 1. Similarly as in FIG. 5, only optical devices in the illumination beam path are represented. Likewise as in FIGS. 2 to 5, no optical devices in the observation beam path or mechanical devices for guiding or holding the optical devices are represented. The cross-sectional plane represented is parallel to the longitudinal axis 18 of the endoscope 10.

Similarly as in the embodiment of FIG. 5, the light guide 30 has no curvature in the vicinity of its light exit surface 32. Similarly as in the embodiments of FIGS. 2 to 4, a lens 36 is provided for collimating the illumination light emerging from the light exit surface 32 of the light guide 30. Furthermore, a fixed curved reflective surface 42 and a moveable planar reflective surface 52 are provided. The moveable planar reflective surface 52 and the fixed curved reflective surface 42 are arranged in such a way that illumination light emerging from the light exit surface 32 of the light guide 30 and collimated by the lens 36 first strikes the moveable planar reflective surface 52 and is reflected thereby. The illumination light reflected by the moveable planar reflective surface 52 strikes the fixed curved reflective surface 42 and is reflected thereby.

The moveable planar reflective surface 52 is moveable in a direction 56 parallel or essentially parallel to the longitudinal axis 18 of the endoscope 10. Depending on the position of the moveable planar reflective surface 52, illumination light reflected thereby strikes different regions of the fixed curved reflective surface 42. Owing to the curvature of the fixed reflective surface 42, the illumination light is shone by the fixed curved reflective surface 42 into different solid angle ranges depending on the position of the moveable planar reflective surface 52. Two different positions of the moveable planar reflective surface 52 are shown in FIGS. 6 and 7. Furthermore, the solid angle ranges into which the illumination light is shone are indicated by contours of a respective illumination light cone 60. Similarly as in the embodiment of FIG. 4, the illumination light cone 60 has a constriction 61 owing to the concave configuration of the fixed curved reflective surface 42.

Figure 8:
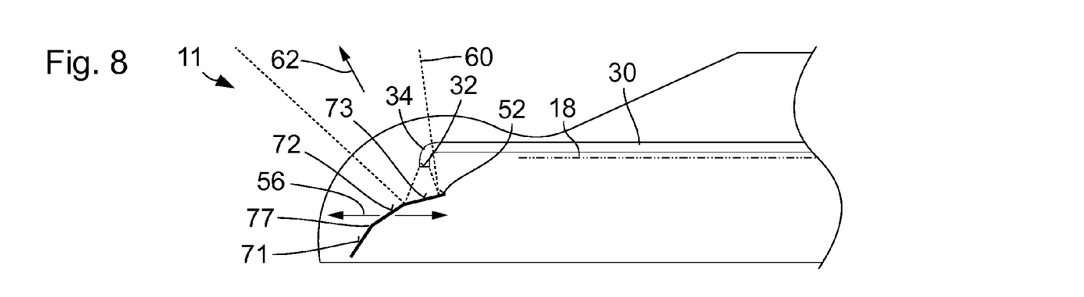
FIG. 8 shows a schematic representation of the distal end of another embodiment of an endoscope.

FIG. 8 shows a schematic representation of another embodiment of the distal end of an endoscope, in particular of the endoscope 10 explained above with the aid of FIG. 1. In some features, the embodiment of FIG. 8 resembles the embodiments of FIGS. 2 to 7, in particular the embodiment of FIGS. 2 and 3. In particular, a reflective surface 52 moveable in a direction 56 is provided. Illumination light emerging from a light exit surface 32 of a light guide 30 is shone in different directions 62 depending on the position of the moveable reflective surface 52.

The embodiment of FIG. 8 differs from the embodiment of FIGS. 2 and 3 particularly in that the moveable reflective surface 52 is not smooth. The reflective surface 52 comprises a plurality of planar or essentially planar sections 71, 72, 73. In the cross section represented in FIG. 8, the sections 71, 72, 73 of the moveable reflective surface 52 are contiguous. Between the sections 71, 72, 73, the moveable reflective surface 52 respectively has a bend 77.

The sections 71, 72, 73 of the moveable reflective surface 52 may be curved in a direction perpendicular to the plane of the drawing of FIG. 8. In particular, the sections 71, 72, 73 are concavely curved in said direction, in order to reduce the cross section of the illumination light bundle. Alternatively, the sections 71, 72, 73 of the moveable reflective surface 52 may respectively have a configuration in the shape of a dome or a saddle. Unlike in the representation of FIG. 8, steps and/or gaps may be provided between the sections 71, 72, 73 of the moveable reflective surface 52.

Figure 9:
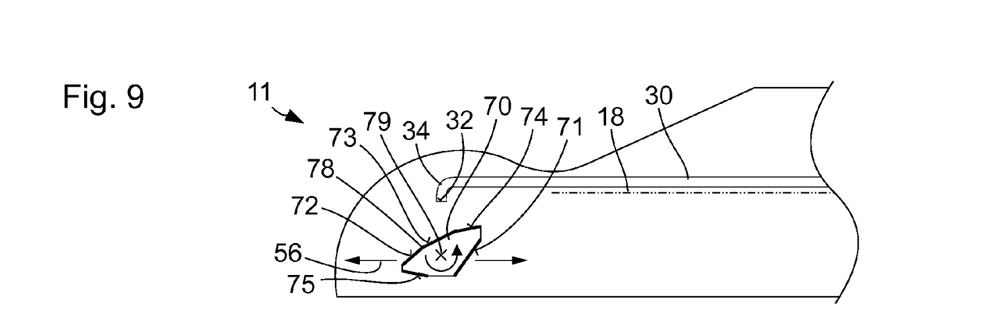
FIG. 9 shows a schematic representation of the distal end of another embodiment of an endoscope.
Figure 10:
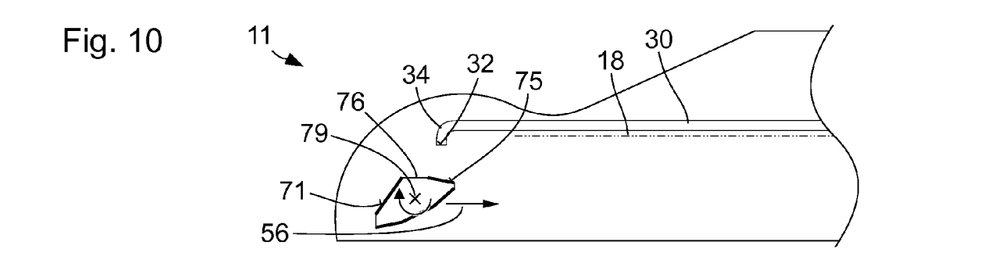
FIG. 10 shows a further schematic representation of the distal end of FIG. 9.

FIGS. 9 and 10 show schematic representations of another embodiment of the distal end of an endoscope, in particular of the endoscope 10 explained above with the aid of FIG. 1. In some features, the embodiment of FIGS. 9 and 10 resembles the embodiments of FIGS. 2 to 8, in particular the embodiment of FIG. 8. In particular, a reflective surface moveable in a direction 56, which has a plurality of sections 71, 72, 73, 74, 75, is provided.

In contrast to the representations of FIGS. 2 to 8, the illumination light cone 60 and the illumination direction 62 are not shown in FIGS. 9 and 10, so as not to overburden the representation. For those skilled in the art, however, the directions in which the sections 71, 72, 73, 74, 75 of the moveable reflective surface reflect illumination light, which emerges from the light exit surface 32 of the light guide 30, are readily apparent.

The sections 71, 72, 73, 74, 75 of the moveable reflective surface are arranged on a mirror carrier 70. The embodiment of FIGS. 9 and 10 differs from the embodiment of FIG. 8 particularly in that the mirror carrier 70 with the sections 71, 72, 73, 74, 75 of the reflective surface is linearly moveable in the direction 56 and pivotable or rotatable about an axis 79. In particular, the mirror carrier 70 is provided and formed in order to be used in two orientations. One of the two orientations is respectively shown in FIG. 9 and FIG. 10.

In the orientation represented in FIG. 9, the mirror carrier 70 with the reflective surface 52 can be displaced in the direction 56. In the position of the mirror carrier 70 as represented in FIG. 9, illumination light emerging from the light exit surface 34 of the light guide 30 predominantly or exclusively strikes the third section 73 of the reflective surface 52. In other positions of the mirror carrier 70 which can be achieved solely by linear displacement, the illumination light predominantly or exclusively strikes the second section 72 or the fourth section 74 of the reflective surface 52.

In the orientation and position of the mirror carrier 70 as represented in FIG. 10, illumination light emerging from the light exit surface 32 of the light guide 30 predominantly or exclusively strikes the fifth section 75 of the reflective surface 52. In the orientation represented in FIG. 10, the mirror carrier 70 can be displaced in the direction 56 to such an extent that illumination light emerging from the light exit surface 32 predominantly or exclusively strikes the first section 71 of the reflective surface.

Regarding FIGS. 9 and 10 together, it can be seen that the sections 71, 72, 73, 74, 75 in the respectively provided orientation of the mirror carrier 70 have different inclinations, that is to say they make different angles with the longitudinal axis 18 of the endoscope 10. In the orientation of the mirror carrier 70 as represented in FIG. 10, the surface normal of the first section 71 of the reflective surface makes a comparatively small angle with the longitudinal axis 18. In the orientation of the mirror carrier 70 as represented in FIG. 10, the surface normal of the fifth section 75 of the reflective surface makes a comparatively large angle with the longitudinal axis 18. The angle which the surface normals of the second section 72, the third section 73 and the fourth section 74 make with the longitudinal axis 18 of the endoscope in the orientation shown in FIG. 9 lie between the other two angles. By rotating the mirror carrier 70 into one of the two orientations represented in FIGS. 9 and 10 and displacing it in the direction 56, five different illumination directions can therefore be adjusted in the example represented.

In the example represented in FIGS. 9 and 10, not all immediately adjacent sections 71, 72, 73, 74, 75 of the reflective surface are directly contiguous. Rather, for example, between the first section 71 and the fifth section 75 of the reflective surface 52 there is a gap 76 in which, in particular, the mirror carrier 70 is not reflectively coated. Alternatively, the mirror carrier 70 may also have a reflective coating in the gap 76. Between the second section 72, the third section 73 and the fourth section 74, the reflective surface respectively merely has a bend 78.

Unlike in the representations in FIGS. 9 and 10, the sections 71, 72, 73, 74, 75 of the reflective surface may be curved, similarly as described in connection with the embodiment of FIG. 8. Furthermore, unlike in the representations in FIGS. 9 and 10, merely a smooth section of the reflective surface may be provided in each orientation of the mirror carrier 70.

Figure 11:
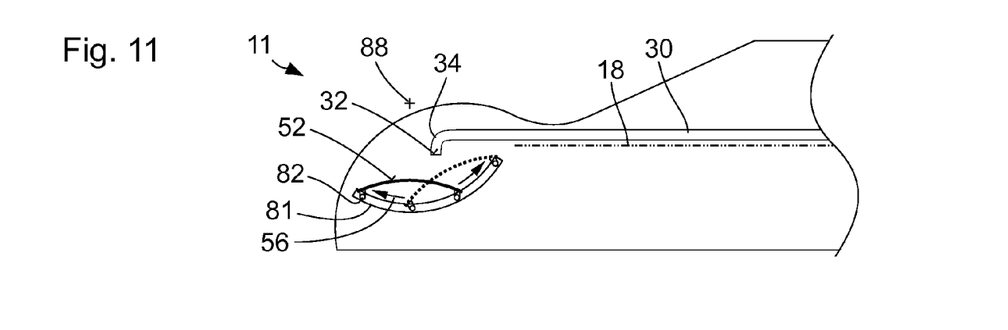
FIG. 11 shows a schematic representation of the distal end of another embodiment of an endoscope.

FIG. 11 shows a schematic representation of another embodiment of the distal end of an endoscope, in particular of the endoscope 10 explained above with the aid of FIG. 1. In some features, the embodiment of FIG. 11 resembles the embodiments of FIGS. 2 to 7, in particular the embodiment of FIGS. 2 and 3. In particular, a smooth, curved and moveable reflective surface 52 is provided.

The embodiment of FIG. 11 differs from the embodiment of FIGS. 2 and 3 particularly in that the moveable reflective surface 52 is moveable along a curved path. The curved path is defined by a curved rail 81. The reflective surface 52 is mechanically coupled, in particular rigidly connected, to a plurality of guide elements 82. The guide elements 82 are guided in or on the rail 81. The rail 81 is, for example, formed by a groove or a web. In particular, two parallel rails 81 are provided on opposite sides of the reflective surface 52.

FIG. 11 represents two positions of the reflective surface 52, in which the regions of the reflective surface 52 respectively facing the light exit surface 32 of the light guide 30 are orientated differently. Similarly as in the embodiment of FIGS. 2 and 3, different illumination directions can therefore be adjusted by displacing the reflective surface along the rail 81.

In the example represented, the rail 81 has a configuration in the form of a circle arc. The center of curvature 88 of the rail 81 lies outside the shaft of the endoscope. Alternatively, the rail 81 has a varying curvature, the center of curvature lying outside the shaft of the endoscope in particular at least for one section of the rail 81. Furthermore, a separate straight or curved rail 81 may be provided for each sliding block 82.

Rails similar to the rail 81 represented in FIG. 11, but in particular in a straight configuration, may also be used in the embodiments of FIGS. 2 to 10 in order to guide the reflective surface.

Some features of the embodiments represented above with the aid of FIGS. 2 to 11 may be combined differently than in the embodiments. For example, the moveable curved reflective surfaces 52 of the embodiments of FIGS. 2 to 4, 8 and 11 and the moveable planar reflective surface 42 and/or the fixed curved reflective surface 52 of the embodiment of FIGS. 6 and 7 may also be arranged on transparent bodies similarly as in the embodiment of FIG. 5. In the embodiment of FIG. 5 as well, the fixed curved reflective surface 52 and/or the moveable curved reflective surface 42 may be configured as mirrors, in a similar way to the reflective surfaces of the embodiments of FIGS. 2 to 4 and 6 to 11, the illumination light being reflected at an exposed reflective layer or, before and after reflection, merely passing through a thin transparent layer.

Furthermore, collimation of the illumination light emerging from the light exit surface 32 of the light guide 30 may be brought about by other measures in all embodiments. Alternatively, collimation of the illumination light may be entirely obviated. Furthermore, the illumination light may be concentrated, that is to say the cross section of the illumination light bundle may be reduced in the vicinity of the reflective surface 52 or 42. In particular, the illumination light bundle may have a constriction, or a waist, at or close to the fixed reflective surface 42 and/or at or close to the moveable reflective surface 52.

In all embodiments, the curved reflective surface 52 or 42 may likewise be curved in a direction perpendicular to the represented plane of the drawing. In particular, the curved reflective surface 52 in the embodiments of FIGS. 2, 3 and 5 respectively has a negative Gaussian curvature K, that is to say the configuration of a saddle surface. In particular, the curved reflective surfaces 52 or 42 in the embodiments of FIGS. 4, 6, 7 and 11 respectively have a positive Gaussian curvature K>0, that is to say a configuration in the shape of a dome. By such a configuration of the curved reflective surface 52 or 42, the extent of the illumination light bundle 60 immediately optically downstream of the curved reflective surface 52 or 42 can be reduced in a direction perpendicular to the planes of the drawing of FIGS. 2 to 11, in order to save on installation space in the illumination beam path.

In the embodiment of FIGS. 2 to 4, the light exit surface of the lens 36 is the closest light exit surface optically upstream of the curved reflective surface 52. In other words, the light exit surface of the lens 36 is the last light exit surface through which illumination light passes before it strikes the moveable reflective surface 52. In the embodiments of FIGS. 2 to 4, the surface normal of the light exit surface 32 of the light guide 30, the average surface normal of the light exit surface of the lens 36 and the symmetry axis of the lens 36 are perpendicular or essentially perpendicular to the longitudinal axis 18 of the endoscope 10.

In the embodiment of FIG. 5, the light exit surface 43 of the fixed transparent body 40 is the closest light exit surface optically upstream of the curved reflective surface 52. In other words, the light exit surface 43 of the fixed transparent body 40 is the last light exit surface through which illumination light passes before it strikes the moveable reflective surface 52. In the embodiment of FIG. 5, the surface normal of the light exit surface 43 of the fixed transparent body 40 is perpendicular to the longitudinal axis 18 of the endoscope 10.

Alternatively, in the embodiments of FIGS. 2 to 5 and 8 to 11, the propagation direction of the illumination light and/or the surface normals of the light exit surface 32 of the light guide 30, or the light exit surface 43 of the fixed transparent body 40, can make an angle with the longitudinal axis 18 of the endoscope 10 which is less than 90 degrees, similarly as in the embodiment of FIGS. 6 and 7.

In all embodiments, a light-emitting diode or another light source having a light exit surface may be provided instead of a light guide 30 at the distal end 11 of the endoscope 10. In all embodiments of FIGS. 2 to 11, the endoscope 10 may have properties and features differing from the explanation with the aid of FIG. 1.

Figure 12:
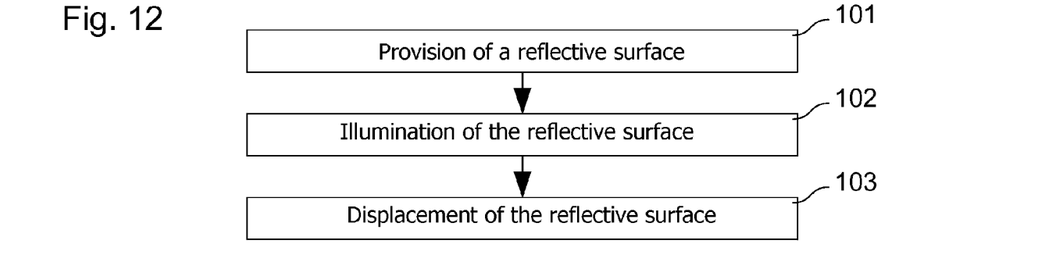
FIG. 12 shows a schematic flow chart of a method for adjusting the illumination direction of an endoscope.

FIG. 12 shows a schematic flow chart of a method for adjusting the illumination direction of an endoscope. The method may, in particular, be carried out with the endoscopes which are explained above with the aid of FIGS. 2 to 11. Alternatively, however, the method may also be carried out with endoscopes which have properties differing from the embodiments of FIGS. 2 to 11. Nevertheless, references from FIGS. 2 to 11 will be used below by way of example.

In a first step 101, a reflective surface 52 is provided for reflecting illumination light for the illumination of an object observed by means of the endoscope 10. In a second step 102, the reflective surface 52 is illuminated with illumination light which emerges from a light exit surface 32, in particular from a light exit surface 32 of a light guide 30, a light exit surface 43 of a transparent body 40 or of a light source. In particular, the illumination light strikes the reflective surface 52 from a direction which is not parallel to the longitudinal axis 18 of the endoscope, not parallel to the pivot axis of the viewing direction and not parallel to the pivot axis of the illumination direction.

In a third step 103, the reflective surface 52 is displaced in order to adjust the illumination direction. In this case, the reflective surface is guided in particular by a straight or curved linear guide 81, 82.

REFERENCES

10 endoscope
11 distal end of the endoscope 10
12 proximal end of the endoscope 10
14 shaft of the endoscope 10
15 first coupler
16 second coupler
18 longitudinal axis of the endoscope 10
20 surface of a window component
21 first extreme viewing direction (0 degrees)
22 second extreme viewing direction (120 degrees)
28 pivot axis of the viewing direction
29 angle range of the viewing directions
30 light waveguide
34 light exit surface of the light waveguide 30 curvature of the light waveguide in the vicinity of its light exit surface 32
36 lens
40 fixed transparent body
41 light entry surface of the fixed transparent body 40
42 fixed reflective surface
43 light exit surface of the fixed transparent body 40
48 photoluminescent body
50 moveable transparent body
51 light entry surface of the moveable transparent body 50
52 moveable reflective surface
53 light exit surface of the moveable transparent body 50
56 direction in which the reflective surface 52 is moveable
60 illumination light cone
61 constriction of the illumination light cone 60
62 illumination direction
70 mirror carrier
71 first section of the reflective surface 52
72 second section of the reflective surface 52
73 third section of the reflective surface 52
74 fourth section of the reflective surface 52
75 fifth section of the reflective surface 52
76 gap between the fifth section 75 and the first section 71
77 bend between the first section 71 and the second section 72
78 bend between the second section 72 and the third section 73
79 axis about which the reflective surface 52 is pivotable
81 rail
82 guide element
88 center of curvature of the rail 81
101 first step
102 second step
103 third step

The invention claimed is:
1. An endoscope having an adjustable illumination direction, comprising:
 a reflective surface reflecting illumination light for illumination of an object observed by means of the endoscope, the reflective surface being moveable in order to adjust the illumination direction;
 a linear guide for guiding the reflective surface along a straight path;
 a transparent body having a light exit surface for exposure of the reflective surface to illumination light and for directing or deviating the illumination light;

wherein a line of intersection of the reflective surface with a plane which is parallel to two adjustable illumination directions of the endoscope is convexly curved.

2. The endoscope as claimed in claim 1, wherein the reflective surface is moveable in a direction which makes an angle of less than 45 degrees with a longitudinal axis of the endoscope.

3. The endoscope as claimed in claim 1, wherein the endoscope is formed to shine the illumination light onto the reflective surface from a direction which is non-parallel to a longitudinal axis of the endoscope.

4. The endoscope as claimed in claim 1, wherein a surface normal of the light exit surface is non-parallel to a longitudinal axis of the endoscope and non-parallel at least either to a pivot axis of the illumination direction or to a pivot axis of a viewing direction.

5. The endoscope as claimed in claim 1, wherein the reflective surface comprises a first section and a second section, with at least either the first section and the second section merging non-smoothly into one another or the section lines of the first section and the second section being oppositely curved with a plane which is parallel to two adjustable illumination directions of the endoscope.

6. A method for adjusting an illumination direction of an endoscope, comprising:
   providing a reflective surface to reflect illumination light for illumination of an object observed by means of the endoscope, wherein a line of intersection of the reflective surface with a plane which is parallel to two adjustable illumination directions of the endoscope is convexly curved;
   providing a transparent body having a light exit surface for exposure of the reflective surface to illumination light and for deviating the illumination light; and
   guiding the reflective surface along a straight path in order to adjust the illumination direction.

7. The endoscope as claimed in claim 1, wherein the transparent body is a prism.

8. An endoscope, comprising:
   a transparent body having a light exit surface from which illumination light emerges, the light exit surface being configured to direct or deviate the illumination light;
   a reflective surface configured to reflect the illumination light emerging from the light exit surface, so as to illuminate an object; and
   a guide configured to move the reflective surface in a direction parallel to a longitudinal axis of the endoscope, so as to adjust a direction of the illumination light reflected by the reflective surface;
   wherein a line of intersection of the reflective surface with a plane which is parallel to two adjustable illumination directions of the endoscope is convexly curved.

* * * * *